United States Patent
Pinza et al.

(10) Patent No.: US 7,056,538 B2
(45) Date of Patent: Jun. 6, 2006

(54) DISINFECTANT SOLUTION BASED ON SODIUM HYPOCHLORITE, AND PROCESS FOR PREPARING IT

(75) Inventors: Mario Pinza, Corsico (IT); Marcello Marchetti, Rome (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 0 days.

(21) Appl. No.: 10/485,105

(22) PCT Filed: Jul. 23, 2002

(86) PCT No.: PCT/EP02/08338

§ 371 (c)(1),
(2), (4) Date: Jun. 22, 2004

(87) PCT Pub. No.: WO03/013250

PCT Pub. Date: Feb. 20, 2003

(65) Prior Publication Data

US 2004/0232381 A1 Nov. 25, 2004

(30) Foreign Application Priority Data

Aug. 3, 2001 (IT) .................... MI2001A1702

(51) Int. Cl.
*A01N 59/00* (2006.01)
*C01B 11/06* (2006.01)

(52) U.S. Cl. ............. 424/662; 424/665; 252/186.21; 252/187.26; 252/187.31

(58) Field of Classification Search .............. None
See application file for complete search history.

(56) References Cited

U.S. PATENT DOCUMENTS

| 4,990,334 A | | 2/1991 | Longino et al. | |
| 5,273,678 A | * | 12/1993 | Deroux et al. | ......... 252/187.26 |
| 5,624,636 A | | 4/1997 | Schwartz | |

FOREIGN PATENT DOCUMENTS

| EP | 0 471 129 | | 2/1992 |
| FR | 2 593 704 | | 8/1987 |
| JP | 08031779 A | * | 2/1996 |
| JP | 8-164189 | | 6/1996 |

OTHER PUBLICATIONS

JPO machine translation of JP 08-16189-A.*
JPO machine translation of JP 08-031779-A.*
Hawley's Condensed Chemical Dictionary, (2002, 14th Edition) (John Wiley & Sons, Inc., New York), "concentration," pp. 290; "isotonic," pp. 633.*
Official Monographs/Sodium, US Pharmacopoeia 24, p. 1535.
Sally F. Bloomfield, et al., The Pharmaceutical Journal, pp. 153-157 Aug. 3, 1985.
Drinking Water and Health; vo. 7: Disinfectants and Disinfectant By-Products (1987), pp. 99-104, (National Academy Press, Washington, DC) http://www.nap.edu/openbook/0309037417/html/99.html.
Drinking Water Substance Priority List, http://www.hc-sc.gc.ca/ehp/ehd/bch/water_quality/priority_Ist.htm Nov. 8, 2000.

* cited by examiner

*Primary Examiner*—Matthew A. Thexton
(74) *Attorney, Agent, or Firm*—Oblon, Spivak, McClelland, Maier & Neustadt, P.C.

(57) ABSTRACT

Sodium hypochlorite disinfectant solution having a pH of between 10.1 and 10.7 and comprising from 0.021 to 5.76% (w/v) of sodium hypochlorite and, relative to the said amount of sodium hypochlorite, not more than 2% of sodium chlorate.

8 Claims, No Drawings

DISINFECTANT SOLUTION BASED ON SODIUM HYPOCHLORITE, AND PROCESS FOR PREPARING IT

The present invention relates to a disinfectant solution based on sodium hypochlorite and to a process for preparing it.

Throughout the present description and the claims, unless otherwise specified, the term "solution" always refers to an aqueous solution.

The bactericidal properties of sodium hypochlorite solutions have been known since 1820. Above all in France, in the period of the First World War, they were also widely used for the medical treatment of war injuries.

Even today, they are widely used as disinfectants for environments, surfaces, surgical instruments, various objects and injures.

The disinfectant activity of sodium hypochlorite solutions depends to a large extent on the bactericidal activity of hypochlorous acid and, thus, on its presence in the solutions.

The efficiency of the activist is influenced by the temperature, the contact time, the type and concentration of the micro-organisms and, above all, the pH. Since the dissociation constant of hypochlorous acid to 25° C. is pKa=7.49, it results that when the hypochlorite solution comes into contact with bodily fluids, the pH is modified and tends to approach neutrality, and thus the ratio between the ionized species and neutral species tend to become equal. Now, although hypochlorite is a bland disinfectant compared with hypochlorous acid, it acts as a reserve.

EP-A-0 471 129 relates to a solution of sodium hypochlorite which is useful as an antiseptic. The solution contains sodium hypochlorite in a quantity sufficient for 4 to 6 grams per liter of active chlorine, a pH regulator In a quantity sufficient to yield a pH greater than 10 and less than or equal to 10.5 and purified water in a quantity sufficient to yield 1 liter of solution.

U.S. Pat. No. 5,624,636 aims at improving the disinfection of dental impressions following removal from the patient's mouth and before entering the dental laboratory to prevent contamination. It Involves the use of a pH-adjusted hypochlorite solution, which is highly effective in killing microorganisms, and also relatively inexpensive. The disinfectant solution causes no damage to the impression, no loss of accuracy, and does not destroy the details on the impression surface. The solution has a pH of from 9 to 11 and has a sodium hypochlorite content of from 0.05% to about 1.05%.

U.S. Pat. No. 4,440,334 discloses a germicidal solution for sanitizing the human epidermis without irritation. The solution is a homogeneous blend of glycerol, sodium hypochlorite, inert ingredients, soft water, scented oil, and isopropyl alcohol, having a pH of 9.8 to about 10.1. The solution may be applied to a towelette and sealed in a hermetically sealed pouch for later use.

One of the problems associated with sodium hypochlorite disinfectant solutions is that their composition cannot be predetermined at will since the industrial methods for producing hypochlorite give solutions in which the sodium hypochlorite is accompanied by side products and starting materials. Thus, since the said industrial solutions are the only sources of hypochlorite that are available for preparing the said disinfectant solutions, the said disinfectant solutions will necessarily also contain a certain amount of the said side products and starting materials already present in the industrial hypochlorite solution used.

The production of sodium hypochlorite is based on the dismutation of molecular chlorine in sodium hydroxide solution.

This reaction, also known as "chlorination of alkali", proceeds according to the following reaction scheme (I):

$$Cl_2 + 2\ NaOH \rightarrow NaClO + NaCl + H_2O \qquad (I)$$

The industrial process more commonly involves the addition of chlorine to an excess of sodium hydroxide.

Solutions containing about 15.70–20.93% (w/v) of sodium hypochlorite [equivalent to 15.00–20.00% (w/v) of active chlorine] are thus obtained, also containing a substantially equivalent amount of sodium chloride and an excess of free bases, generally less than 1% (expressed as NaOH), which gives a pH of about 12.5–13.5 and acts as stabilizer.

Throughout the present description and the claims, this type of solution will be referred to as a concentrated solution.

Concentrated sodium hypochlorite solutions have various industrial uses and, when used in unmodified form or suitably diluted, are also used for disinfecting articles. However, the said solutions cannot be used in unmodified form for clinical and/or veterinary disinfection since they are not tolerated by the skin or mucous membranes.

Moreover, its high pH value also prevents the formation of hypochlorous acid.

Hypochlorite disinfectant solutions are therefore prepared by diluting a concentrated solution with added mineral salts which act as buffers to reduce its pH and thus improve its tolerability and bactericidal activity.

In particular, typical disinfectant solutions for topical use are as follows:

Dakin's solution (*French Pharmacopoeia* 8th edition, p. 1059) containing about 0.5% sodium hypochlorite, the same percentage of sodium chloride, 1.5% sodium bicarbonate and 1 mg/100 ml of potassium permanganate; and the skin disinfecting solution described in the US Pharmacopoeia (*USP* 24, p. 1535), which contains 0.02–0.032% sodium hypochlorite, 1.02 g/l monobasic sodium phosphate, 17.61 g/l dibasic sodium phosphate and has a pH of between 7.8 and 8.2. Although it is not mentioned by the USP, since this solution is prepared from a concentrated sodium hypochlorite solution, it also contains at least 0.02–0.032% sodium chloride.

However, reducing the pH of these solutions has the drawback of reducing the stability of the sodium hypochlorite and so, depending on their composition, these solutions can only be stored from a minimum of a few days to a maximum of a few months (S. F. Bloomfield, T. J. Sizer, "Pharm. J. (1985), 153–157).

The said disinfectant solutions must therefore be prepared by the user at the time of use or slightly beforehand.

Specifically, even if stored with care, the abovementioned sodium hypochlorite disinfectant solutions obtained by diluting a concentrated solution with added buffers undergo a spontaneous decomposition which produces sodium chlorate, sodium chloride and small amounts of sodium chlorite.

The formation of sodium chlorate and sodium chlorite also has the drawback that these products have toxicological properties (*Drinking Water and Health, Disinfectants and Disinfectant By-products.* volume 7, National Academy Press, Washington, D.C., 1987) which are such that regulations have been drawn up therefor (*Priority list of substances that may require regulation under the safe drinking water act*; EPA, 1991, (56), 9, 1470–1474, *EPA 40 CFR part*

9 141, 142 *National Primary Drinking Water Regulations: Disinfectant and Disinfection Byproduct, Final Rule*, Dec. 16, 1998).

The only known method for preparing relatively dilute sodium hypochlorite solutions that do not have the drawbacks of the solutions obtained by diluting a concentrated solution with added buffers is that of the electrolysis of sodium chloride solutions in diaphragm-free electrolytic cells so as to allow the products that are gradually formed by the electrolysis to react together. The dilute sodium hypochlorite disinfectant solutions thus obtained contain an excess of sodium chloride and have a pH of between 10 and 10.5.

These solutions, subsequently diluted without pH correction or with the possible addition of small amounts of pH correctors, are well tolerated by the skin and mucous membranes. In addition, they are stable for at least two years and can therefore be dispensed in pharmacies.

Typical examples of possible pH correctors are sodium bicarbonate, sodium tetraborate and monobasic and dibasic sodium phosphate mixtures.

A disinfectant solution of this type has been sold for many years under the brand name AMUCHINA™ and has the following composition:

| | |
|---|---|
| sodium hypochlorite: | 1.15% (w/v), equivalent to 1.1% active chlorine; |
| sodium chloride: | 18% (w/v); |
| sodium chlorate: | 17–26%, relative to the abovementioned amount of sodium hypochlorite; |
| pH | 10–10.5. |

Hereinbelow, the sodium hypochlorite solutions obtained by the electrolysis of sodium chloride in diaphragm-free electrolytic cells will be referred to as "electrolytic solutions".

Despite the abovementioned advantages, electrolytic solutions contain a large excess of sodium chloride and this may be a drawback in certain types of application such as, for example, rendering water fit for consumption.

The sodium chlorate contained arises due to the fact that, besides the spontaneous decomposition, a secondary reaction of anodic oxidation of the hypochlorite is associated with the primary electrolytic reaction, to a certain extent $(6ClO^-+3H_2O \rightarrow 2ClO_3^-+4Cl^-+6H^++3/2O_2+6e^-)$.

However, the main drawback of electrolytic solutions consists of the high costs of the plants required to produce them and of the costs incurred in their management.

In addition, the electrolytic method cannot be used to produce relatively concentrated solutions [>3% (w/v)] since this would initiate secondary electrolytic reactions which would lead to a reduction in the yield and, above all, to the production of excessively high levels of sodium chlorate, thus harming the quality of the solutions.

Therefore, notwithstanding the many attempts made over more than a century, an inexpensive method for preparing a sodium hypochlorite disinfectant solution that is stable for at least two years, does not contain an excess of sodium chloride, has high bactericidal activity and is well tolerated by the skin and mucous membranes has still not been found.

Hitherto, these objectives have been considered as mutually incompatible since, as already seen, an alkaline pH ensures the stability but has a harmful effect on the tolerability by the skin and mucous membranes and reduces the bactericidal power. On the other hand, at neutral pH, the bactericidal power is high, but stability is low.

French patent 2 593 704 describes a stabilized and dilute 0.5% sodium hypochlorite solution in which the stabilization is achieved by adding an amount of monosodium phosphate which is sufficient to lower the pH to a value of 9.6–10. According to the said document, the abovementioned disinfectant solution is well tolerated by the skin but has a stability of only six months.

Now, it has been found, surprisingly, that the dilution of a concentrated sodium hypochlorite solution and the addition of dilute hydrochloric acid until the pH is 10.1–10.7 makes this solution well tolerated by the skin and mucous membranes without reducing its stability, without forming appreciable amounts of sodium chlorate and without the addition of other ionic solutes.

Typically, a sodium hypochlorite disinfectant solution thus obtained has the following characteristics:

| | |
|---|---|
| sodium hypochlorite: | 0.021–5.76% (w/v), equivalent to 0.020–5.50% (w/v) of active chlorine; |
| sodium chlorate: | 1.7% relative to the abovementioned amount of sodium hypochlorite; |
| water: | qs 100 ml |
| pH | 10.1–10.7 |

This solution is novel since it differs from the other known hypochlorite disinfectant solutions, obtained by diluting a concentrated solution with added buffers, in terms of the pH value and the absence of buffers. In addition, it differs from electrolytic solutions in terms of the levels of sodium chlorate.

In a first aspect thereof, the present invention therefore relates to a sodium hypochlorite disinfectant solution, characterized in that it has a pH of between 10.1 and 10.7 and comprises from 0.021 to 5.76% (w/v) of sodium hypochlorite and, relative to the said amount of sodium hypochlorite, not more than 2% of sodium chlorate.

Preferably, the amount of sodium hypochlorite included in the disinfectant solution of the present invention ranges from 0.52% to 2.09% (w/v), equivalent to 0.50–2.00% of active chlorine.

Advantageously, the pH of the disinfectant solution of the present invention is between 10.1 and 10.5.

Typically, the disinfectant solution of the present invention which comprises from 0.021 to 5.76% (w/v) of sodium hypochlorite, also comprises from 0.015 to 4% (w/v) of sodium chloride.

The disinfectant solution of the present invention may be readily made isotonic by adding a suitable amount of sodium chloride.

In addition, a suitable amount of a colorant that is compatible with the components of the solution may also be added to the disinfectant solution of the present invention. A typical example of a suitable colorant is potassium permanganate.

The addition of dilute hydrochloric acid to pH 10.1–10.7 is sufficient to obtain a hypochlorite disinfectant solution that has all the advantages that will be listed hereinbelow. However, after the pH has been partially corrected with dilute hydrochloric acid, for example to 11, a small amount of another compound capable of correcting the pH, for example from 11 to 10.5, may be added. Typical examples of such compounds are: sodium tetraborate, sodium bicarbonate, sodium carbonate, sodium monohydrogen phosphate, sodium dihydrogen phosphate and the like.

In a second aspect thereof, the present invention relates to a process for preparing a sodium hypochlorite disinfectant solution, in which the said process comprises the dilution of a concentrated sodium hypochlorite solution, characterized in that the pH of this solution is brought to a value of between 10.1 and 10.7 by adding dilute hydrochloric acid.

Typically, before being subjected to the process of the present invention, the concentrated solution comprises from 15.70 to 20.93% (w/v) of sodium hypochlorite and its pH is about 13.

Preferably, the concentration of hydrochloric acid in the dilute solution used in the process of the present invention ranges from 0.01 to 1 mol/liter and preferably 0.1–1 mol/liter.

The sodium hypochlorite disinfectant solution according to the present invention has the following advantages;
- it is economical since it is readily and quickly prepared by means of very simple apparatus;
- it is well tolerated like Dakin's solution and the other analogous solutions described in the pharmacopoeias and like the electrolytic solutions;
- it is stable like electrolytic solutions and is therefore suitable for sale in pharmacies as a ready-to-use solution;
- it is readily adaptable to various requirements in terms of concentrations and addition of other solutes;
- it has high bactericidal efficacy; and
- it contains very small amounts of sodium chlorate.

The examples which follow serve to illustrate the invention without, however, limiting it.

EXAMPLE 1

Solution 1

750 ml of distilled water were added to 58.97 ml of a solution, containing 19.5% (w/v) of sodium hypochlorite, 18% (w/v) of sodium chloride and less than 10 ppm of sodium chlorate, and having a pH of 13.

1N HCl was then added until the pH was 10.5.

Finally, distilled water was added to make 1000 ml.

The solution thus obtained contained 1.15% (w/v) of sodium hypochlorite [equivalent to 1.1% (w/v) of active chlorine] and 1.06% (w/v) of sodium chloride.

EXAMPLES 2–3

Solutions 2 and 3

To check the effect of the pH correctors, the process was performed exactly as described in Example 1, except that the pH of the starting solution was first brought to 11 with 1N HCl and then to 10.5 with sodium tetraborate (Solution 2) or sodium bicarbonate (Solution 3).

EXAMPLE 4

Solution 4

To check the effect of the sodium chloride, the process was performed exactly as described in Example 1, except that the content of sodium chloride was then raised to 18% (w/v).

TEST 1

Stability

The stability of Solutions 1–4 was studied for 75 days in an environment having a temperature of 40° C. and a relative humidity of 75% and for 63 days at ambient temperature (about 24° C.).

The study was performed in comparison with an electrolytic solution (Comparative Solution) of pH 10.3 and containing 1.15% (w/v) of sodium hypochlorite (equivalent to 1.1% of active chlorine), 18% sodium chloride and, relative to the abovementioned amount of sodium hypochlorite, about 26% (w/v) of sodium chlorate.

The results are illustrated in Tables I and II below.

TABLE I

| | (T = 40° C.; R.H. = 75%) | | | | | |
|---|---|---|---|---|---|---|
| Solution | PH | | Sodium hypochlorite | | Chlorates (ppm) | |
| No. | initial | 75 days | initial | 75 days | initial | 75 days |
| 1 | 10.5 | 10.1 | 1.15 | 0.98 | 162 | 1046 |
| 2 | 10.5 | 10.1 | 1.15 | 0.90 | 134 | 1413 |
| 3 | 10.5 | 10.2 | 1.15 | 0.93 | 146 | 1272 |
| 4 | 10.5 | 9.8 | 1.15 | 0.85 | 157 | 1548 |
| Comparative | 10.3 | 9.6 | 1.15 | 0.80 | 2640 | 4128 |

TABLE II

| | (Ambient temperature) | | | | | |
|---|---|---|---|---|---|---|
| Solution | PH | | Sodium hypochlorite | | Chlorates (ppm) | |
| No. | initial | 63 days | initial | 63 days | initial | 63 days |
| 1 | 10.5 | 10.3 | 1.15 | 1.14 | 162 | 251 |
| 2 | 10.5 | 10.4 | 1.15 | 1.15 | 134 | 281 |
| 3 | 10.5 | 10.4 | 1.15 | 1.14 | 146 | 272 |
| 4 | 10.5 | 10.4 | 1.15 | 1.15 | 157 | 295 |
| Comparative | 10.3 | 10.2 | 1.15 | 1.11 | 2640 | 2950 |

These data prove that the disinfectant solution of the present invention behaves like the comparative electrolytic solution which, as is known, is stable for at least 2 years. Thus, it may reasonably be deduced that the solution of the invention will also be stable for at least two years.

TEST 2

Bactericidal Activity

The bactericidal activity of the disinfectant solution of Example 1 was compared with that of the electrolytic solution mentioned in the preceding Test 1, according to standard UNI EN 1040.

Strains of *Staphylococcus aureus* ATCC 6538 and *Pseudomonas aeruginosa* ATCC 15442 were subjected, for 5 minutes at 20° C., to solutions containing five different concentrations of sodium hypochlorite, respectively: 28.75 ppm, 57.5 ppm, 115 ppm, 230 ppm and 460 ppm, obtained by diluting the solutions under investigation.

The interpretation of the results according to standard UNI EN 1040 showed that both the solutions induce a logarithmic reduction $>10^5$ in the bacterial vitality.

In conclusion, the two solutions under investigation showed themselves to have the same bactericidal activity at the same concentrations.

The invention claimed is:

1. A sodium hypochlorite disinfectant solution, comprising:
0.021 to 5.76% (w/v) of sodium hypochlorite,
from 0.015 to 4% (w/v) of sodium chloride, and
water;

wherein the solution is buffer-free and contains no more than 2% of sodium chlorate relative to the sodium hypochlorite; and wherein the solution has a pH that ranges from 10.1 to 10.7.

2. The solution according to claim 1, wherein the sodium hypochlorite ranges from 0.52% to 2.09% (w/v).

3. The solution according to claim 1 or claim 2, wherein the pH is between 10.1 and 10.5.

4. The solution according to claim 1 or claim 2, further comprising a colorant.

5. The solution according to claim 3, further comprising a colorant.

6. A process for preparing the sodium hypochlorite disinfectant solution as claimed in claim 1, which comprises:

diluting a concentrated sodium hypochlorite solution to obtain a dilute sodium hypochlorite solution and adding dilute hydrochloric acid to the dilute sodium hypochlorite solution to obtain the sodium hypochlorite disinfectant solution having a pH between 10.1 and 10.7.

7. The process according to claim 6, wherein the concentrated hypochlorite solution has a pH of 13 and comprises from 15.70 to 20.93% (w/v) of sodium hypochlorite.

8. The process according to claim 6 or claim 7, wherein the dilute hydrochloric acid solution comprises 0.01–1 mol/liter of hydrochloric acid.

* * * * *